United States Patent [19]

Gould

[11] 4,054,518

[45] Oct. 18, 1977

[54] APPARATUS AND METHODS FOR SANITIZING SEWAGE EFFLUENT AND COMPOSITIONS FOR USE THEREIN

[76] Inventor: Lawrence P. Gould, 608 Cumberland Ave., Syracuse, N.Y. 13210

[21] Appl. No.: 237,862

[22] Filed: Mar. 24, 1972

[51] Int. Cl.$^2$ .................................................. C11D 7/54
[52] U.S. Cl. ......................................... 210/61; 210/62; 210/199; 424/148
[58] Field of Search .......................... 210/62, 61, 199; 424/148, 249, 19, 22; 21/107, 58

[56] References Cited

U.S. PATENT DOCUMENTS

| | | | |
|---|---|---|---|
| 2,792,345 | 5/1957 | Hulsebosch et al. | 210/62 X |
| 3,164,524 | 1/1965 | Fand et al. | 424/148 X |
| 3,296,069 | 1/1967 | Kowalski | 210/62 X |
| 3,488,420 | 1/1970 | Keast et al. | 210/62 X |
| 3,749,672 | 7/1973 | Golton et al. | 210/62 X |

Primary Examiner—Frank A. Spear, Jr.
Attorney, Agent, or Firm—Carella, Bain, Gilfillan & Rhodes

[57] ABSTRACT

Apparatus and methods for sanitizing sewage effluent comprising supporting a plurality of solid members in a conduit in fluid-flow intercepting relationship to sewage effluent flowing therethrough, the said solid members being soluble in the effluent to release a bactericidal agent at a relatively constant rate at least in part as a function of the mass rate of effluent flow thereover and the surface area of said members exposed to effluent flow, the said solid members being supported in the conduit by means such as a rack in which the solid members are positioned generally in a row extending along the path of effluent flow, each solid member extending across a substantial portion of the flow-responsive, varying depth of effluent in the conduit such that the surface area of said member exposed to effluent flow is at least in part a function of the mass-rate of effluent flow in the conduit such that the quantity of bactericidal agent released varies at least in part as a function of the mass rate of effluent flow through the conduit, the said solid members consisting essentially of compacted trichloroisocyanuric acid and an additive selected from the group consisting of boric acid and calcium stearate, the additive appearing in quantities relative to the trichloroisocyanuric acid just sufficient to generate a relatively constant release of available chlorine over a desired period of time.

10 Claims, 1 Drawing Figure

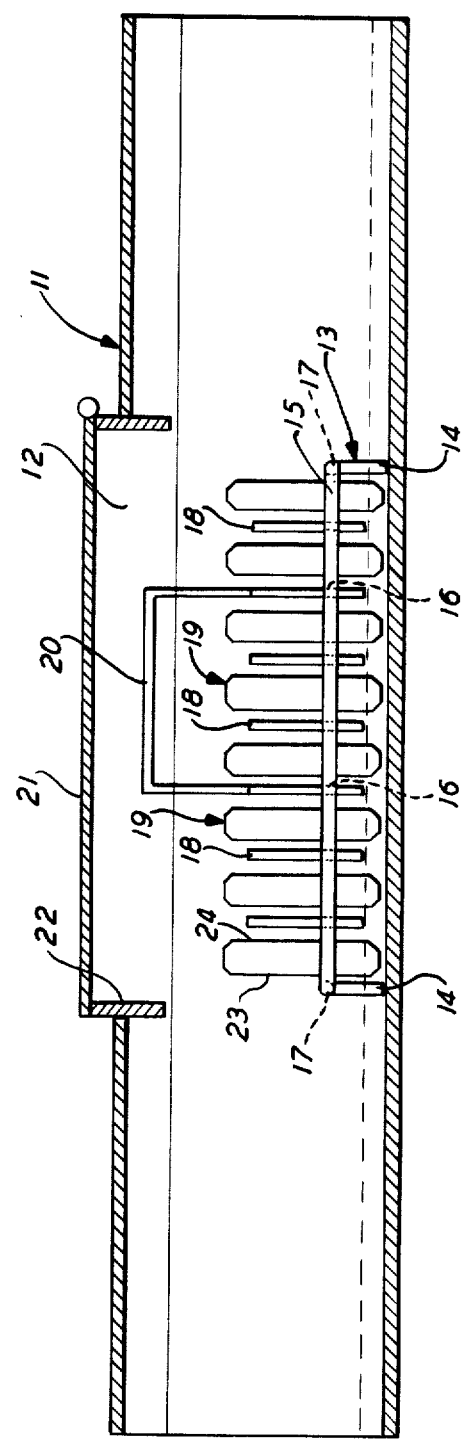

4,054,518

APPARATUS AND METHODS FOR SANITIZING SEWAGE EFFLUENT AND COMPOSITIONS FOR USE THEREIN

BACKGROUND OF THE INVENTION

In relatively small sewage disposal systems, on the order of 100,000 gallons per day or less, sewage effluent from a sand filter or settling tank is generally passed to some public water-way. Chlorine is added to the sewage effluent to destroy odor, color and bacteria to insure against pollution of the public water-way.

Normally, liquid chlorine or a hypochlorite solution is employed as a bactericidal agent for the sewage effluent. Available equipment is costly and requires constant attendance. In northern climates when hypochlorite solutions are employed, they frequently freeze and the effluent remains untreated.

The present invention relates to apparatus and methods to treat sewage effluent which is inexpensive and needs no constant attendance. The apparatus comprises a rack fabricated of a material impervious to both sewage effluent and a chlorine releasing bactericidal agent, preferably fabricated of plastic containing tablets of trichloroisocyanuric acid. The rack is seated within a conduit for the flow of sewage effluent. The tablets are positioned in a row generally along the direction of effluent flow. The tablets extends generally transversely across a substantial portion of the conduit so that the greater the depth of effluent in the conduit, the greater the surface area of tablets exposed thereto.

The number of tablets employed in a row is a function of the demand for bactericidal agent which must be satisfied. In periods of relatively high effluent flow rate, the tablets may be nearly or completely submerged thereby dissolving at a maximum rate. However, at low flow periods only a small portion of the tablet would be exposed and a correspondingly low rate of dissolution experienced.

The bactericidal agent is trichloroisocyanuric acid which, in the presence of water, forms the familiar hypochlorite solution leaving cyanuric acid which is tasteless, odorless, colorless and non-toxic. Nevertheless, the trichloroisocyanuric acid must be mixed with an additive to insure a constant rate of solution otherwise, the trichloroisocyanuric acid tablets tend to dissolve erratically.

SUMMARY OF THE INVENTION

A flowing effluent sanitizer comprising a conduit having effluent flowing therethrough, the depth of effluent in the conduit being substantially a function of the mass-rate of effluent flow therethrough, a plurality of solid members in the conduit in fluid flow intercepting relationship to effluent flowing therethrough, means for supporting said solid members generally in a row extending along the path of effluent flow, each solid member extending across a substantial portion of the varying depth of effluent flow in the conduit, the said solid members being soluble in the effluent to release a bactericidal agent at a relatively constant rate at least in part as a function of the mass-rate of effluent flow in the conduit, each said solid member consisting essentially of compacted trichloroisocyanuric acid and an additive selected from the group consisting of boric acid and a combination of boric acid and calcium stearate in relative ratios by weight of 1:4 to 4:1 the additive appearing in quantities relative to the trichloroisocyanuric acid just sufficient to achieve the desired rate of dissolution, the boric acid appearing in quantities no less than approximately 1% by weight of the trichloroisocyanuric acid.

A solid soluble sanitizing table consisting essentially of a self-sustaining compacted mass of trichloroisocyanuric acid and an additive selected from the group consisting of boric acid and a combination of boric acid and calcium stearate, the combination of boric acid and calcium stearate appearing in relative quantities of approximately 4 parts by weight calcium stearate to 1 part by weight boric acid to 4 parts by weight boric acid to 1 part by weight calcium stearate, the additive appearing in quantities just sufficient to achieve the desired rate of dissolution of the trichloroisocyanuric acid, the boric acid appearing in quantities no less than approximately one percent by weight of the trichloroisocyanuric acid.

A method for sanitizing flowing sewage effluent comprising supporting a plurality of solid members in a conduit in fluid flow intercepting relationship to effluent flowing therethrough, the said solid members being soluble in the effluent to release a bactericidal agent at a relatively constant rate at least in part as a function of the mass-rate of effluent flow thereover and the surface area of said members exposed to effluent flow, positioning the said solid members in the conduit with respect to effluent flow such that the surface area of said members exposed to effluent flow is substantially a function of the mass-rate of effluent flow in the conduit, passing effluent through the conduit over varying portions of the surface area of said solid members to release desired variable quantities of bactericidal agent at least in part as a function of the mass-rate of effluent flow through the conduit, each said solid member consisting essentially of compacted trichloroisocyanuric acid and an additive selected from the group consisting of boric acid and a combination of boric acid and calcium stearate in relative ratios by weight of 1:4 to 4:1, the additive appearing in quantities relative to the trichloroisocyanuric acid just sufficient to achieve the desired rate of dissolution, the boric acid appearing in quantities no less than approximately, 1% by weight of the trichloroisocyanuric acid.

PREFERRED EMBODIMENT OF INVENTION

The objects and advantages aforesaid as well as other objects and advantages may be achieved by use of the apparatus, methods and compositions hereinafter described, a preferred embodiment of the apparatus of which is illustrated in the drawings in which:

The figure is a side elevational cross-sectional view of a conduit with a tablet supporting rack mounted therein.

Referring now to the drawings in detail, the effluent sewage sanitizer comprises a conduit 11 having a radially enlarged chamber 12. While the chamber has been shown as preferably being radially enlarged, it nevertheless may be the same diameter as conduit 11.

The rack 13 having upstanding end legs 14, 14 and spaced apart longitudinal rails 15, 15 is mounted within the chamber 12. Cross members 16, 16, etc. extend between the rails 15,15 and end members 17, 17 extend between the upstanding legs 14, 14 at both ends of the rack 15. Upstanding spacer ribs 18, 18, etc. are formed on the cross member 16, 16 defining separate spaces for generally upstanding tablets 19, 19 etc. of trichloroisocyanuric acid. A handle 20 is formed on two of the spaced-apart spacer ribs for removal of the rack 13 through a hinged door 21 extending across an opening 22 and the top of the chamber 12.

The tablets 19, 19 are positioned in a row along the axis of the conduit 11 and chamber 12. Additionally, the tablets 19, 19 are dimensioned to extend generally vertically across the diameter of the conduit 11 such that at maximum effluent flow rates in the conduit as indicated by solid line 25, the said tablets are either completely submerged or nearly completely submerged. The lowermost extent of each of the tablets 19 is in close proximity to the bottom of the chamber 12 such that at minimum effluent flow rates as indicated by the broken line 26, the bottom of each tablet 19 is just submerged.

Each of the tablets 19 is generally cylindrical having opposed, generally parallel, flat faces 23 and 24. When positioned in the rack 13, the faces 23 and 24 of each tablet 19 are generally normal to the path of effluent flow in the conduit 12.

Preferably, the conduit 11 and chamber 12 are positioned so that the depth of effluent flowing therein is a function of the mass-rate flow. Thus, the chamber 12 should not be placed in a low spot which would produce pooling of the effluent. In addition, it is also preferable that the chamber 12 not be vertical which might compromise the relationship between effluent flow rate and the depth of effluent in the chamber 12 without elaborate control mechanism.

The periphery of each of the tablets 19 is circular, conforming to the cross-sectional configuration of the better part of the chamber 12. Thus, the area of contact between the tablets 19 and the effluent is approximately a direct function of the depth of the effluent in the chamber 12.

It is essential that the tablets 19 dissolve at a constant rate to release a bactericidal agent. The best bactericidal agent is trichloroisocyanuric acid which is soluble in water to release active chlorine leaving isocyanuric acid as a residue which is odorless, colorless, tasteless and non-toxic.

Dichloroisocyanuric acid is also a good source of active chlorine but is so excessively water soluble that the tablets would necessarily have to be replenished much too frequently. It is also difficult to control the rate of dissolution of dichloroisocyanurate within narrow limits.

The commercially available sodium and potassium salts of trichloroisocyanuric acid are excessively water soluble and are therefore impractical because they are likely to dissolve in a few hours under usual conditions.

Pure trichloroisocyanuric acid tablets tend to dissolve at an erratic rate. It has been found that the use of and addition agent selected from the group consisting of boric acid and calcium stearate when properly compacted under proper conditions produces a tablet which will dissolve at a known, predetermined and relatively constant rate. Either the boric acid alone or the combination of boric acid and calcium stearate can be employed in varying amounts depending upon the rate of dissolution desired. Boric acid alone as an addition agent tends toward higher rates of dissolution than a combination of boric acid and calcium stearate which tends toward lower rates of dissolution.

The addition agent must be very finely divided when mixed with the trichloroisocyanuric acid prior to compaction. It has been found that the addition agent should have a particle size of 200 mesh or smaller for an easily obtained homogenous tablet. If more than 15% boric acid is to be employed, a greater than 200 mesh particle size should be used to prevent air-trapping.

The pressure of tableting has also been found to bear an important relationship to the functional characteristics of the tablet which contains trichloroisocyanuric acid and the addition agent. The tablet pressures is preferably between approximately 2,060 p.s.i. to 2,380 p.s.i. with a pressure of 2320 p.s.i. preferred.

Table I is illustrative of the relative rates of dissolution of three different tablets, each employing a different additive or additive combination in the amount of 5% by weight of the trichloroisocyanuric acid. The dissolution rate is recorded as a function of parts per million of residual chlorine determined by placing each of the tablets in a feeder canister and flushing tap water at 50° Fahrenheit over it at a rate of 28 ounces of water per minute.

TABLE I

| ADDITIVE 5% | BORIC ACID | AL | MG | NA | CARNAUBA WAX | 2½% BORIC ACID 2½% Ca STEARATE |
|---|---|---|---|---|---|---|
| Tablet | | STEARATE | | | | STEARATE |
| I | 378 | 25 | 59 | 200 | 164 | 113 |
| II | 365 | 200 | 188 | 355 | 106 | 113 |
| III | 378 | 95 | 95 | 95 | 95 | 113 |

It may be observed from Table I that various relatively insoluble stearates and waxes substantially retard the rate of dissolution of trichloroisocyanuric acid. However, there is a marked variation from tablet to tablet in the same batch of granular or powdered material compacted which is undesirable. Nevertheless, it has been found that either boric acid or a combination of boric acid and calcium stearate produce tablets which dissolve at a relatively constant rate from tablet to tablet.

Table II is illustrative of the range of relative quantities of boric acid to calcium stearate as it affects the constancy of the rate of dissolution of the table. In compiling the data for Table II, the water flow rate over the tablets was 28 ounces per minute at 68° F. The tableting pressure was 2320 p.s.i.

TABLE II

| TABLET | % BORIC ACID | % CALCIUM STEARATE | ppm Cl |
|---|---|---|---|
| I | 1 | 4 | 60 |
| II | 1 | 4 | 60 |
| III | 1 | 4 | 60 |
| I | 4 | 1 | 70 |
| II | 4 | 1 | 70 |
| III | 4 | 1 | 70 |
| I | 0 | 5 | 200 |
| II | 0 | 5 | 60 |
| III | 0 | 5 | 90 |

The data from Table II demonstrates the calcium stearate alone produces an erratic rate of dissolution from tablet to tablet.

The lower limit of additive employed with trichloroisocyanuric acid has been found to be approximately one percent by weight of the trichloroisocyanuric acid. However, this is a function of the stability of the trichloroisocyanuric acid as affected by the boric acid. There is no fixed upper limit with respect to chemistry other than as the relative quantity of additive increases there is correspondingly less trichloroisocyanuric acid available for bacteriological purposes. Thus, the upper limit is determined by the amount of available chlorine desired from the tablet and the time of dissolution when employing a combination of boric acid and calcium stearate. The lower limit, however, bears a relationship to the constancy of the rate of dissolution and the stability of the trichloroisocyanuric acid. Obviously, calcium stearate which is much less soluble than trichloroisocyanuric acid results in slower rates of dissolution than boric acid alone or combinations of boric acid and calcium stearate since boric acid and trichloroisocyanuric acid have almost the same solubility rate in water.

The following examples are illustrative of usable compositions of trichloroisocyanuric acid and additives when compacted as indicated above.

EXAMPLE I

| CONSTITUENT | PERCENT BY WEIGHT OF TABLET OF ACTIVE INGREDIENTS |
|---|---|
| TCIC | 95% |
| Boric Acid | 5 |

EXAMPLE II

| | |
|---|---|
| TCIC | 95 |
| Boric Acid | 2.5 |
| Calcium Stearate | 2.5 |

EXAMPLE III

| | |
|---|---|
| TCIC | 95 |
| Boric Acid | 1 |
| Calcium Stearate | 4 |

EXAMPLE IV

| | |
|---|---|
| TCIC | 95 |
| Boric Acid | 4 |
| Calcium Stearate | 1 |

I claim:

1. A flowing effluent sanitizer comprising:
   a. a conduit having effluent flowing therethrough, the depth of effluent in the conduit being substantially a function of the mass-rate of effluent flow therethrough,
   b. a plurality of solid members in the conduit in fluid flow intercepting relationship to effluent flowing therethrough,
   c. means for supporting said solid members generally in a row extending along the path of effluent flow,
   d. each solid member extending across a substantial portion of the varying depth of effluent flow in the conduit,
   e. the said solid members being soluble in the effluent to release a bactericidal agent at a relatively constant rate at least in part as a function of the mass-rate of effluent flow in the conduit,
   f. each said solid member consisting essentially of compacted trichloroisocyanuric acid and an additive selected from the group consisting of boric acid and a combination of boric acid and calcium stearate in relative ratios by weight of 1:4 to 4:1 the additive appearing in quantities relative to the trichloroisocyanuric acid just sufficient to achieve the desired rate of dissolution, the boric acid appearing in quantities no less than approximately 1% by weight of the trichloroisocyanuric acid.

2. A flowing effluent sanitizer comprising:
   a. the structure in accordance with claim 1 in which
   b. each solid member is compacted at a pressure of from approximately 2060 p.s.i. to 2380 p.s.i.

3. A flowing effluent sanitizer comprising:
   a. the structure in accordance with claim 1 in which
   b. the additive appears in quantities of approximately 5 percent by weight of the trichloroisocyanuric acid and additive.

4. A solid soluble sanitizing tablet consisting essentially of:
   a. a self-sustaining compacted mass of trichloroisocyanuric acid and
   b. an additive selected from the group consisting of boric acid and a combination of boric acid and calcium stearate,
   c. the combination of boric acid and calcium stearate appearing in relative quantities of approximately 4 parts by weight calcium stearate to 1 part by weight boric acid to 4 parts by weight boric acid to 1 part by weight calcium stearate,
   d. the additive appearing in quantities just sufficient to achieve the desired rate of dissolution of the trichloroisocyanuric acid,
   e. the boric acid appearing in quantities no less than approximately one percent by weight of the trichloroisocyanuric acid.

5. A solid soluble sanitizing tablet consisting essentially of
   a. the composition in accordance with claim 4 in which
   b. the additive appears in quantities no less than approximately one percent by weight of the trichloroisocyanuric acid.

6. A solid soluble sanitizing tablet consisting essentially of
   a. the composition in accordance with claim 4 in which
   b. the additive is a combination of boric acid and calcium stearate in which the boric acid appears in quantities no less than approximately one percent by weight of the combined trichloroisocyanutic acid and additive, and
   d. in which the calcium stearate appears in quantities of no less than approximately 4 percent by weight of the combined trichloroisocyanuric acid and additive.

7. A solid soluble sanitizing tablet consisting essentially of
   a. the composition in accordance with claim 4 which,
   b. the additive is a combination of boric acid and calcium stearate,
   c. the boric acid appearing in quantities of approximately one percent to 4 percent by weight of the trichloroisocyanuric acid and additive,
   d. the calcium stearate appearing in quantities of approximately one percent to four percent of the trichloroisocyanuric acid and additive, and
   e. the additive appearing in quantities of approximately 5 by weight of the trichloroisocyanuric acid and additive.

8. A method for sanitizing flowing sewage effluent comprising:
   a. supporting a plurality of solid members in a conduit in fluid flow intercepting relationship to effluent flowing therethrough,
   b. the said solid members being soluble in the effluent to release a bactericidal agent at a relatively constant rate at least in part as a function of the mass-rate of effluent flow thereover and the surface area of said members exposed to effluent flow,
   c. positioning the said solid members in the conduit with respect to effluent flow such that the surface area of said members exposed to effluent flow is substantially a function of the mass-rate of effluent flow in the conduit,
   d. passing effluent through the conduit over varying portions of the surface area of said solid members to release desired variable quantities of bactericidal agent at least in part as a function of the mass-rate of effluent flow through the conduit, e. each said solid member consisting essentially of compacted trichloroisocyanuric acid and an additive selected from the group consisting of boric acid and a combination of boric acid and calcium stearate in relative ratios by weight of 1:4 to 4:1, the additive appearing in quantities relative to the trichloroisocyanuric acid just sufficient to achieve the desired rate of dissolution, the boric acid appearing in quantities no less than approximately 1% by weight of the trichloroisocyanuric acid.

9. A method for sanitizing flowing sewage effluent comprising:
   a. the procedure in accordance with claim 9, in which
   b. each solid member is compacted at a pressure of from approximately 2060 p.s.i. to 2380 p.s.i.

10. A method for sanitizing flowing sewage effluent comprising:
   a. the procedure in accordance with claim 9, in which
   b. the additive appears in quantities of approximately 5% by weight of the trichloroisocyanuric acid and additive.

* * * * *